US005078126A

United States Patent [19]

Perry

[11] Patent Number: 5,078,126

[45] Date of Patent: Jan. 7, 1992

[54] FLOTATION CONTROLLED SPINAL DECOMPRESSION

[76] Inventor: Leroy R. Perry, 1301 E. Rubio St., W. Los Angeles, Calif. 90034

[21] Appl. No.: 516,453

[22] Filed: Apr. 30, 1990

[51] Int. Cl.⁵ .......... A61F 5/01

[52] U.S. Cl. .......... 128/75; 128/76 R; 128/78

[58] Field of Search .......... 128/75, 76 R, 78; 272/71; 434/254

[56] References Cited

U.S. PATENT DOCUMENTS

| | | | |
|---|---|---|---|
| 95,321 | 9/1869 | Carrigan . | |
| 1,347,913 | 7/1920 | Rink | 128/75 |
| 1,897,810 | 2/1933 | Mallory et al. . | |
| 2,176,722 | 10/1939 | Smith et al. . | |
| 2,825,224 | 3/1958 | Lindenauer et al. . | |
| 3,108,587 | 10/1963 | Das | 128/75 |
| 3,118,441 | 1/1964 | George | 128/75 |
| 3,221,735 | 12/1965 | Goodman | 128/75 |
| 3,512,416 | 5/1970 | Hohwart . | |
| 3,751,031 | 8/1973 | Yamauchi | 272/57 R |
| 3,835,847 | 9/1974 | Smith | 128/75 |
| 3,859,990 | 1/1975 | Simon | 128/75 |
| 3,861,675 | 1/1975 | Hopper | 272/71 |
| 4,247,096 | 1/1981 | Schmitt | 272/71 |
| 4,383,524 | 5/1983 | Boger | 128/75 |
| 4,722,329 | 2/1988 | Kalvag | 128/75 |
| 4,730,606 | 3/1988 | Leininger | 128/75 |

FOREIGN PATENT DOCUMENTS

| | | | |
|---|---|---|---|
| 2303694 | 8/1974 | Fed. Rep. of Germany . | |
| 1139435 | 2/1985 | U.S.S.R. | 128/75 |
| 1292764 | 2/1987 | U.S.S.R. | 128/75 |
| 1466739 | 3/1989 | U.S.S.R. | 128/75 |
| 908550 | 10/1962 | United Kingdom | 128/75 |

*Primary Examiner*—Richard J. Apley
*Assistant Examiner*—L. Thomas
*Attorney, Agent, or Firm*—William W. Haefliger

[57] ABSTRACT

A method of treating a patient having a spinal condition for which traction is recommended which includes: suspending the patient's body to extend generally vertically in a water pool; the suspending including exerting downward pulling on the patient's body, at or below waist level; and the suspending including suspending the patient's body at or above shoulder level, to resist the downward pulling, and thereby create force transmission tending to decompress the patient's spine.

14 Claims, 18 Drawing Sheets

FLOTATION CONTROLLED SPINAL DECOMPRESSION

BACKGROUND OF THE INVENTION

This invention relates generally to exercise and rehabilitation method and equipment, and more particularly, to method an apparatus usable in conjunction with a swimming pool or water body to aid or achieve therapeutic decompression.

The problem of decreasing pressure on the spine, discs, nerve roots and associated anatomy to relieve pain, is a continuing one. There is abundant need for effective apparatus and techniques to achieve and/or facilitate such pain relieving spinal decompression.

SUMMARY OF THE INVENTION

It is a major object of the invention to provide method and apparatus meeting the above need. Basically, the method of the invention includes:

a) suspending the patient's body to extend generally vertically in a water pool, b) the suspending including exerting downward pulling on the patient's body, at or below waist level, c) and the suspending including suspending the patient's body at, above, or below shoulder level, to resist the downward pulling, and thereby create force transmission tending to decompress the patient's spine.

As will appear, the step of exerting downward pull typically includes attaching a weight to the patient's body to hang in the water pool below the body; and the step of suspending the patient's body at above or below shoulder level is effected by suspending the patient's head, shoulders or thorax. Opposite force transmitting tethers may be attached to the patient's legs, waist, or trunk and to the shoulders or head, for these purposes.

It is a further object to provide a support frame to extend above or at a higher level than the patient's head, the upward force transmitting tether being attached to that frame. The latter may be adjustable, vertically, to displace the patient vertically, and thereby adjust his buoyancy in the pool, and adjust the force transmission tending to elongate the spine. Such frame adjustment may be effected horizontally and cyclically, to cyclically vary the force transmission tending to elongate the spine. Controlled therapeutic tensioning of body muscles, and therefore spinal decompression, including cervical, thoracic and lumbar muscles may thereby be achieved, and including a full range of motion movements of extremities to create resistive and isokinetic exercises for shoulders, arms, elbows, wrist, hands, fingers, hips, thighs, knees, calfs, ankles, and feet. In addition, waves may be produced in the water pool to cause cyclic movement of the patient's vertically stretched and suspended body, to aid in spinal decompression.

Added objects, both vertically and horizontally, include the provision of weight means, or flotation body means, or drag chute means pulled in the water, and connected by tethers to the vertical patient or the horizontal swimming patient. Resiliently stretchable band means may also be provided to transmit tether loading, and smoothly vary decompression loading exerted on the spine.

These and other objects and advantages of the invention, as well as the details of an illustrative embodiment, will be more fully understood from the following specification and drawings, in which:

DRAWING DESCRIPTION

FIG. 1 is a side elevation showing body suspension in a pool of water via upward and downward force transmitting tethers;

FIGS. 1*a*-1*g* are like FIG. 1*a* except that FIG. 1*a* shows use of a flotation vest; FIG. 1*b* shows use of a turbulent pool of water; FIG. 1*c* shows use of wrist and ankle weights; FIG. 1*d* shows use of a flotation vest as the sole lifting force means; FIG. 1*e* shows use of a tether; FIG. 1*f* shows use of a surface adjustable weight creating sub-surface force; FIG. 1*g* is a top plan view showing use of multiple tethers; FIG. 1*h* is like FIG. 1*a* but showing backward and forward movement apparatus; FIG. 1*i* is like FIG. 1*h* but showing manipulable elastic bands to enhance the range of motion exercises;

Figure 12:
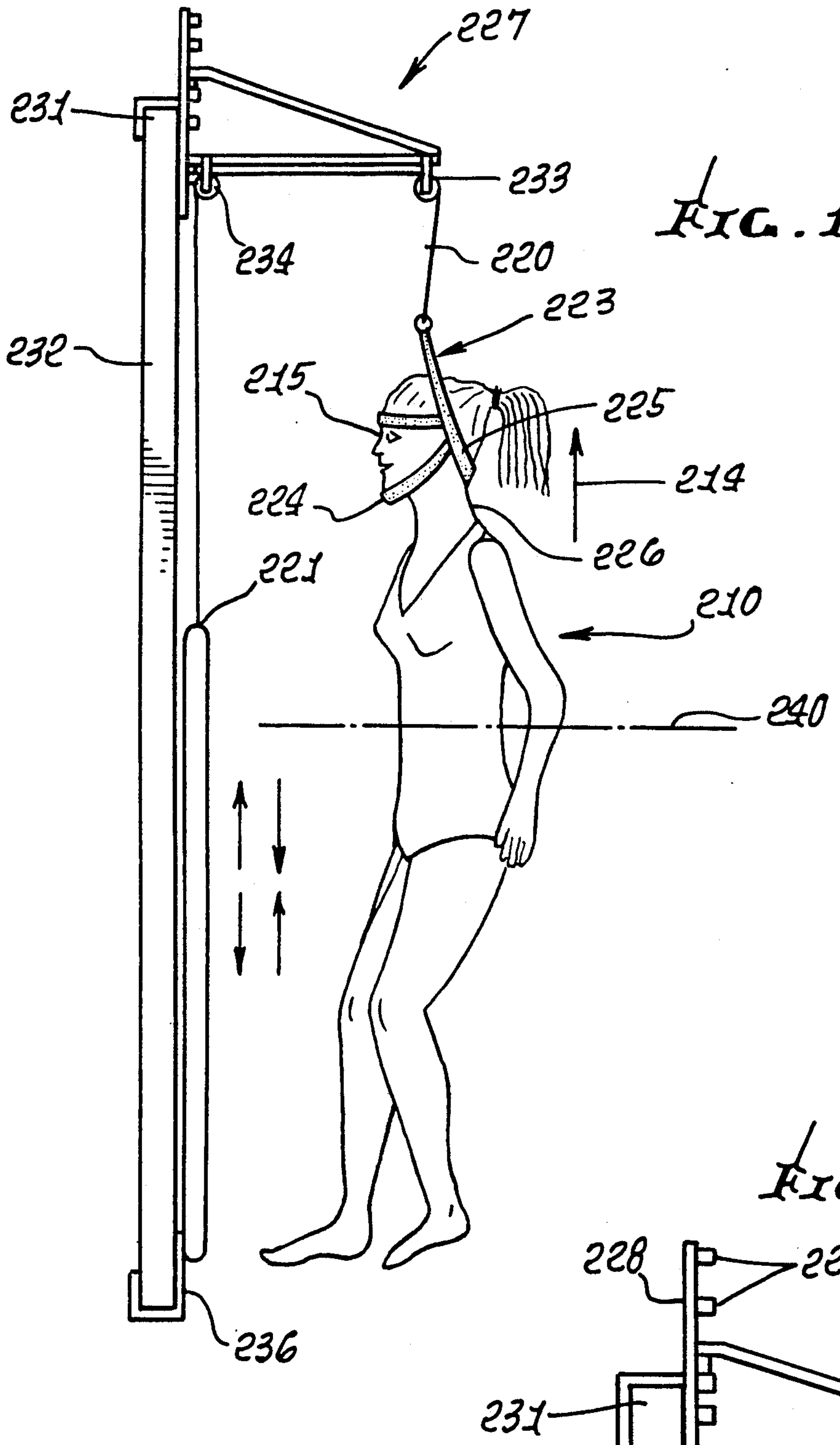
FIG. 12 is a view like FIG. 1 showing suspension of body weight via the head and to a stretchable band.
Figure 12A:
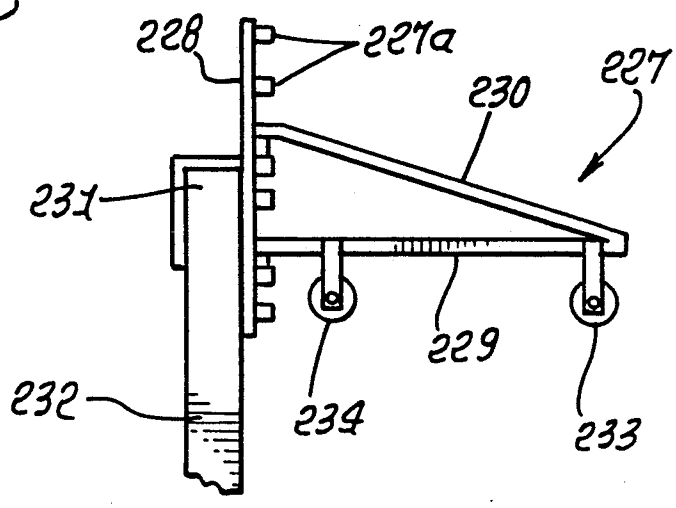

FIG. 12*a* shows a vertically adjustable bracket; and

Figure 13:
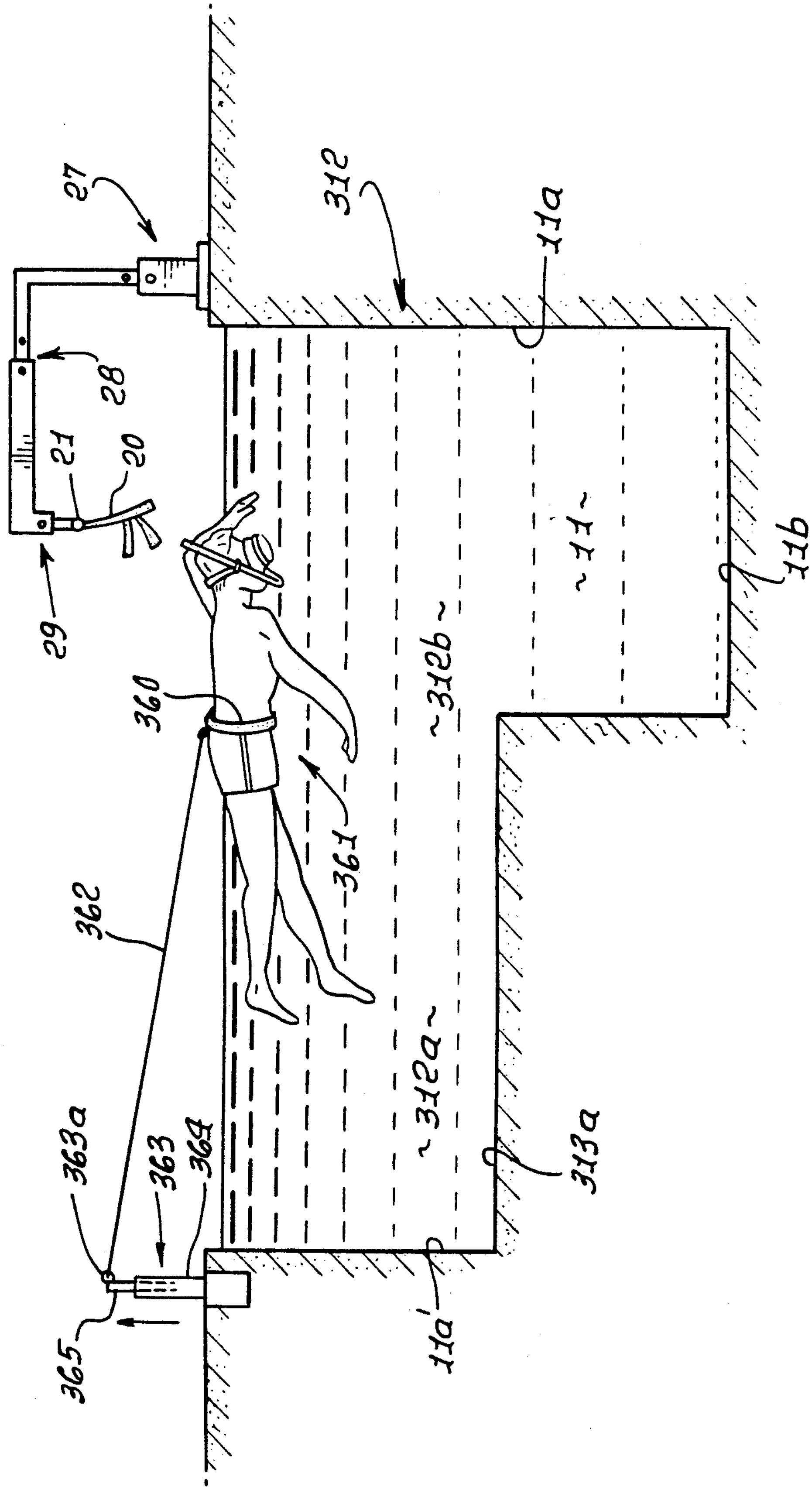

FIG. 13 is an elevation showing a pool adapted for spinal decompression use.

DETAILED DESCRIPTION

Figure 1:
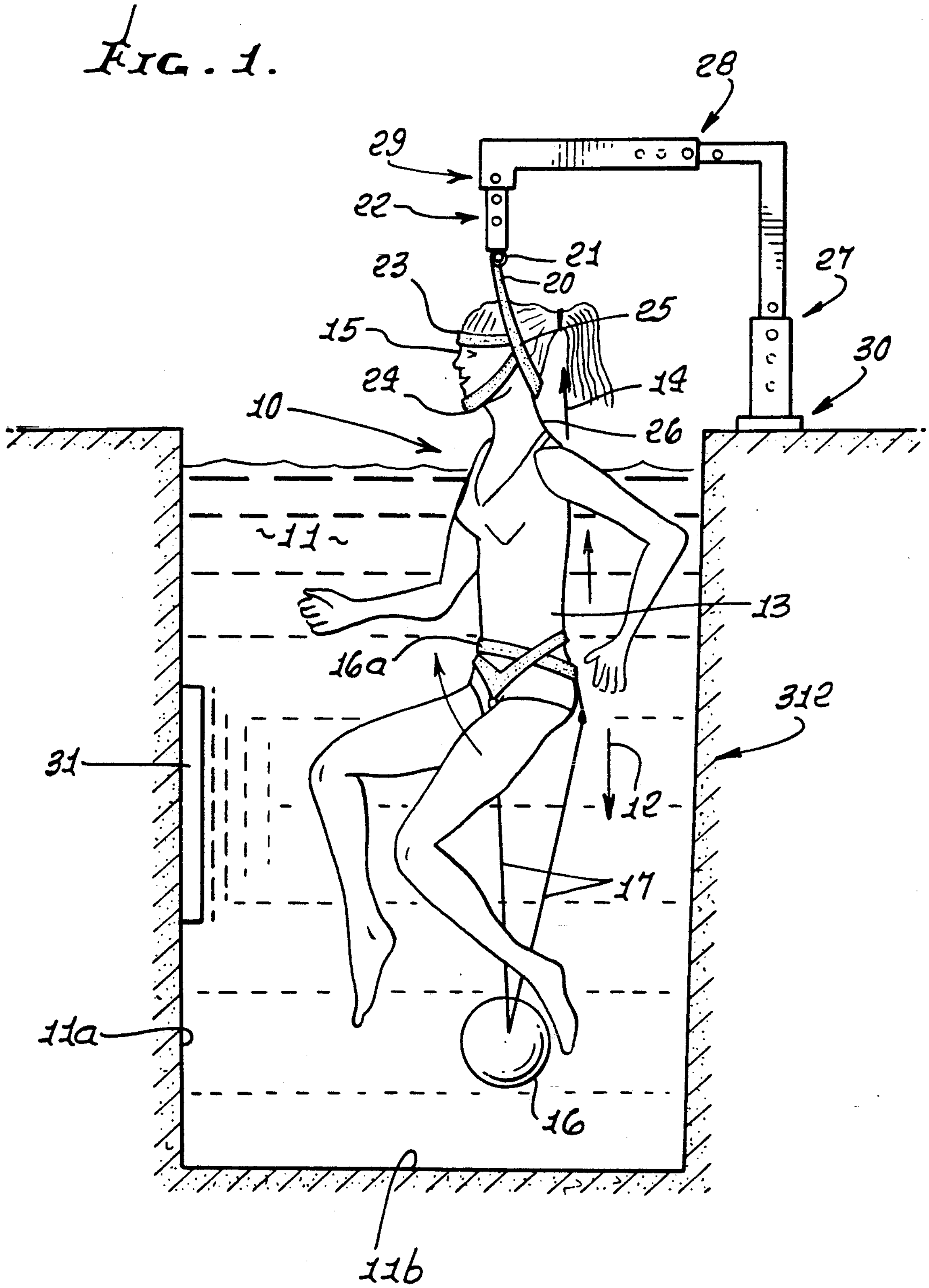

In FIG. 1, a human patient 10 is suspended in a pool of water 11, as in a swimming pool or spa 312 having a wall or walls 11*a*. The pool may comprise a spa with a deep bottom wall 11*b*. Such suspending includes exerting downward loading (see arrow 12) on the body, at or below waist level 13, and suspending the body at or above shoulder level, to resist downward pulling force, i.e., providing an equal and opposite upwardly directed force (see arrow 14) exerted on the head 15. These forces are transmitted through the patient's spine, tending to elongate or decompress the spine.

In the example, a weight 16 is connected via a tether 17 to the waist 13, the weight located below the patient's feet 18 so that kicking of the feet in the pool of water will not result in foot injury. Belt 16*a* attaches tether 17 to the waist.

Suspending of the body above or at shoulder level is effected as by suspending the patient's head. See flexible tether or band 20 attached to the head, and also attached at 21 to a support frame 22. Attachment to the head is effected as by attachment at 23 to the forehead, or at 24 to the underside of the chin, or at 25 to the rear of the head, or to any combination of these. Thus, upward force is transmitted via the upper end of the spine, i.e., at the neck 26.

Figure 2:
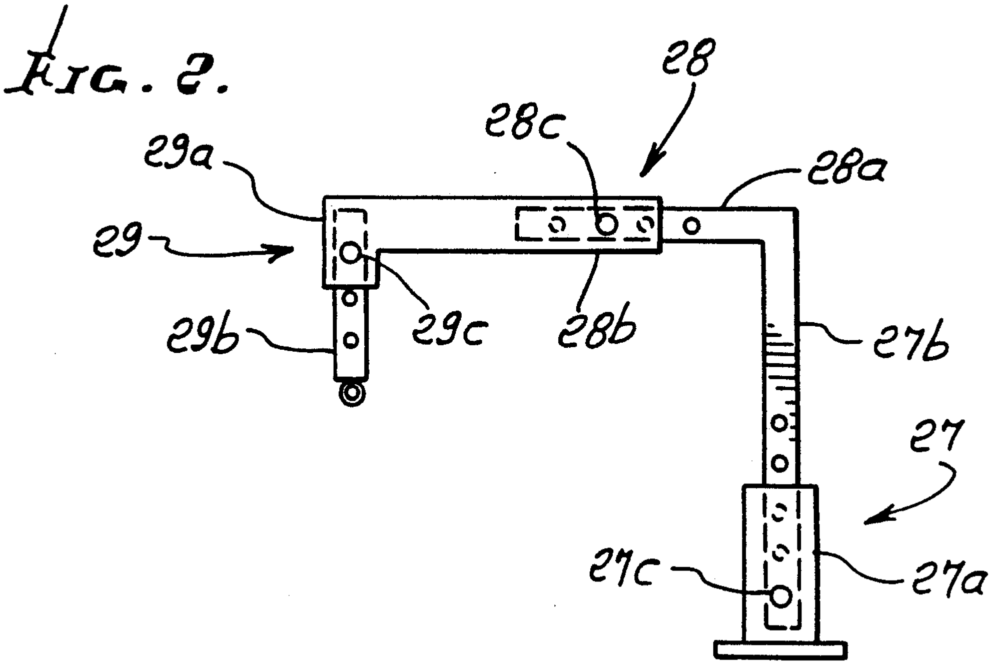
FIG. 2 shows adjustment of a suspension frame.

The illustrated support frame includes end connected members 27-29. Upright member 27 is supported at 30 at pool side; horizontal member 28 is connected at one end to the upper end of member 27; and vertical member 29 is connected at its upper end to member 28. One or more of the support members are adjustable to displace the patient in the pool, varying or adjusting his or her buoyancy in the pool 11 so as to controllably vary the spinal decompression force or forces. See for example FIG. 2 showing telescopically adjustable parts:

27*a* and 27*b* of 27,
28*a* and 28*b* of 28, and
29*a* and 29*b* of 29.

Set screws 27*c*, 28*c*, and 29*c* are tightened to hold the members in their adjusted positions, endwise.

Numeral 31 indicates a wave-producing means in the pool. Such waves sidewardly impact the patient's body to cause gentle body movement, cyclically, during body vertical suspension, to assist in spinal decompression and vertebra relative movement or adjustment and alignment.

Figure 3:
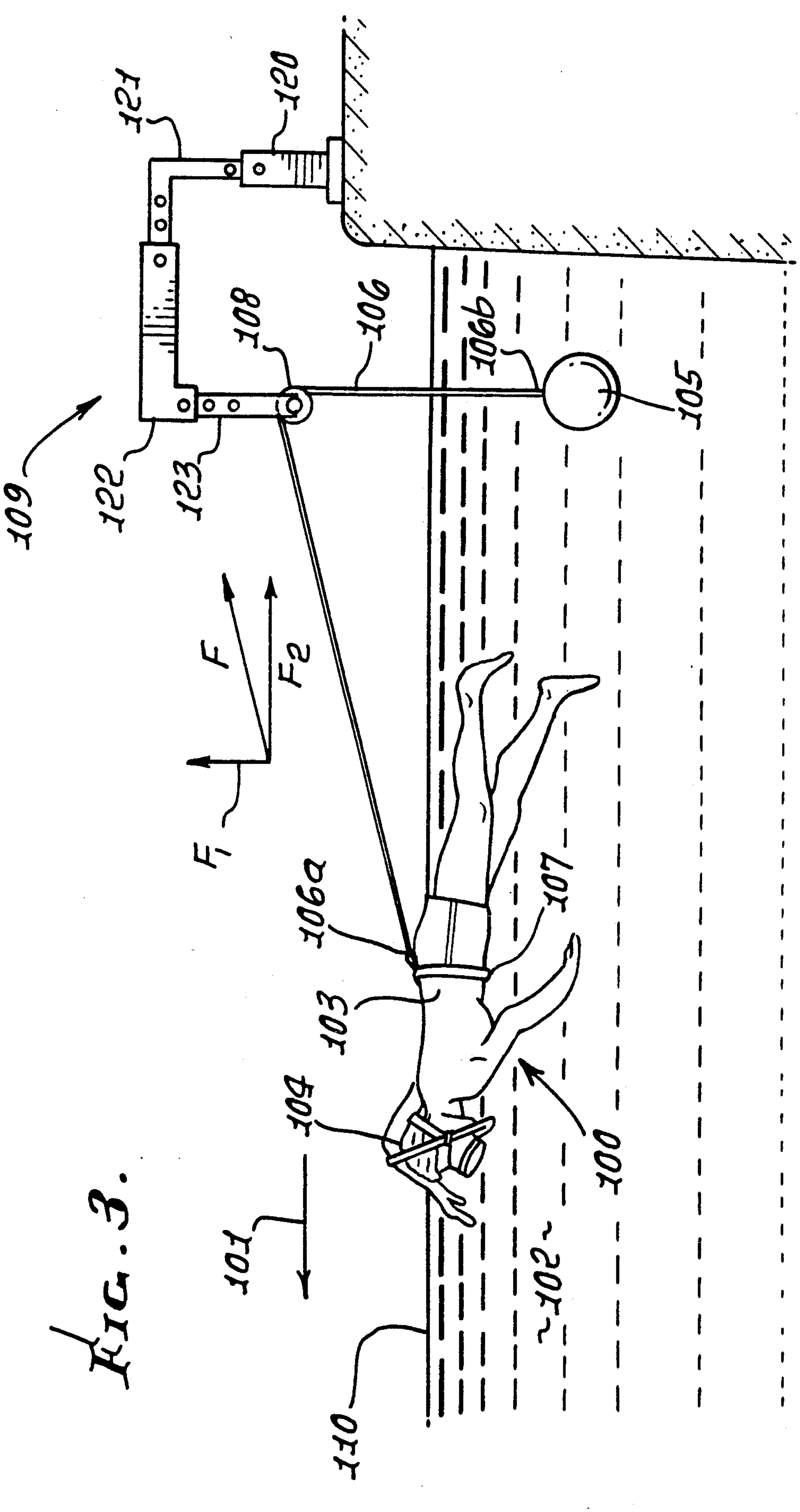
FIG. 3 is an elevation showing another alternate set up of tethered weight and frame apparatus.

In FIG. 3, a patient 100 is shown swimming in leftward direction 101 in water pool 102. The patient is suspended in the pool, as by pulling on the patient's body, at or proximate waist level 103, and in a direction away from the patient's head 104. Further, the patient's body is allowed to bodily move in the pool (as for example horizontally due to swimming), and as against force constantly applied and transmitted to the body to effect such pulling. Note that pulling may be effected by suspending a vertically movable metallic (or other dense material) weight 105 in such a way as to allow horizontal movement of the patient in the pool, the force extended by the weight acting to decompress the spine.

This is accomplished by connecting a tether 106 to transmit force from the weight to the patient's body, at generally waist level, as referred to. As shown, one end 106*a* of this tether is connected to a harness 107 attached about the patient's waist, and to a point at the patient's back; and the opposite end 106*b* of the tether is connected to the weight 105, which is free to move up and down, as in the pool water. A flotation belt may also be used to create greater lift and therefore increased spinal decompression. The tether is directed over a support 108 (for example a pulley) on a frame 109 (which may be the same as the frame described above), and at a level above pool surface level 110, thereby to create a vertically upward force component $F_1$ constantly acting on the patient's waist region to lift the latter and thereby decompress the spine, as the patient swims generally horizontally. His swimming motion also tends to move the spinal vertebrae as the decompression force is exerted, aiding therapeutic realignment and corrective adjustment of the vertebrae and discs therebetween.

As a further feature, the weight is allowed to move up as the patient swims away from the support, maximizing exertive forces, and it is allowed to move down gently, pulling the patient to the right as he decreases exertive force swimming, whereby repetition of weight upward movement can be carried out; further, constant force $F_1$ acting to decompress the spine is at all times exerted. Force $F_2$ tends to pull the patient to the right. Components $F_1$ and $F_2$ combine to provide the force F exerted along the tether, by the weight.

The frame is adjustable at telescopically interconnected sections 120 and 121, and 122 and 123, to elevate or lower the support 108, thereby to vary (increase or decrease) $F_1$ to best suit the patient. Pulley 108 may be connected to a diving board or other pool equipment, or to a hook or "eye" attached to the pool wall or to pool equipment.

The patient may also swim on his back so that connection 106*a* is at his lower abdomen.

FIGS. 4–11 show additional method of force creation acting to elongate the spine, or decompress the spine, or decrease lordosis (sway back). Such techniques are variously beneficial for relief of spinal disc pressure on spinal nerves, relief of nerve and root compression, relief of bulging or herniated discs, and for spine associated nerves and muscular "re-education", and for relief of curvature of the spine (scoliosis).

Figure 4:
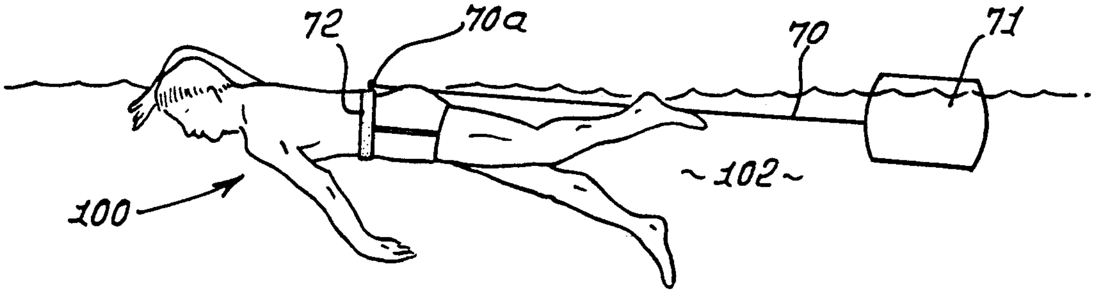
FIG. 4 is a schematic showing tethered attachment of a flotation body to a swimming patient, near the back.
Figure 4A:
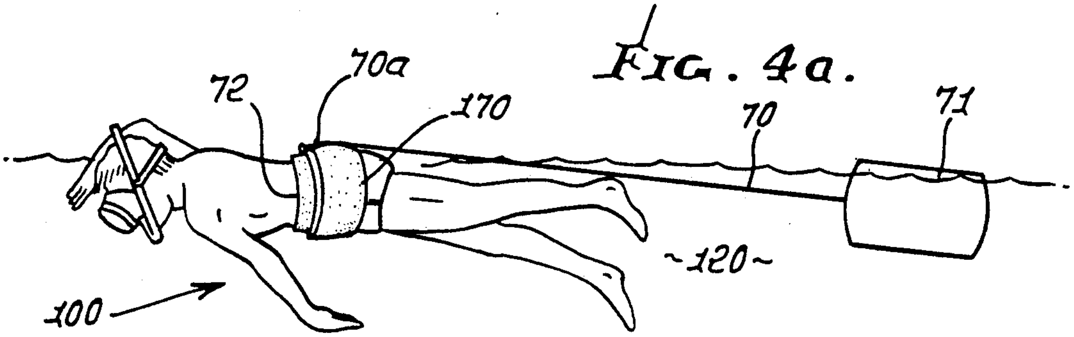
FIG. 4*a* is similar but shows use of a flotation belt.

FIG. 4 shows attachment of a tether 70 between a flotation body (plastic, bladder, etc.) 71 and a harness 72 (such as a belt) about the patient, at waist level. The tether is attached to the harness at 70*a*, i.e., at the patient's back, tending to locally elevate the spine, in decompressing mode.

Figure 6:
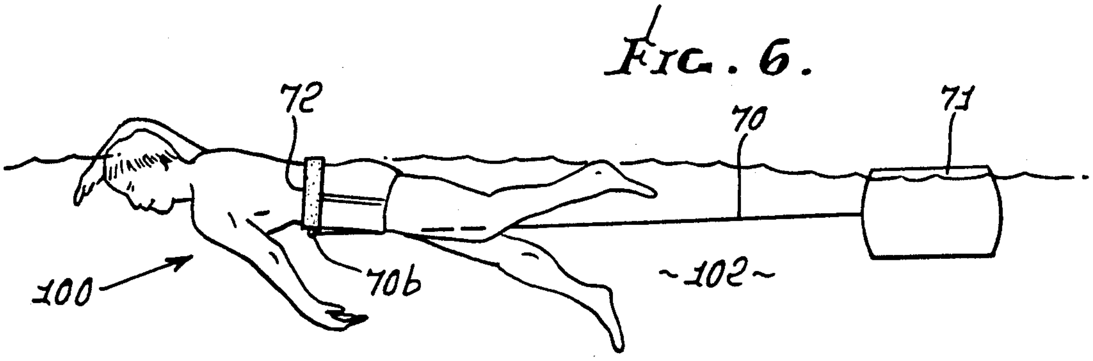
FIG. 6 is a schematic showing tethered attachment of a flotation body to a swimming patient, near the abdomen.
Figure 6A:
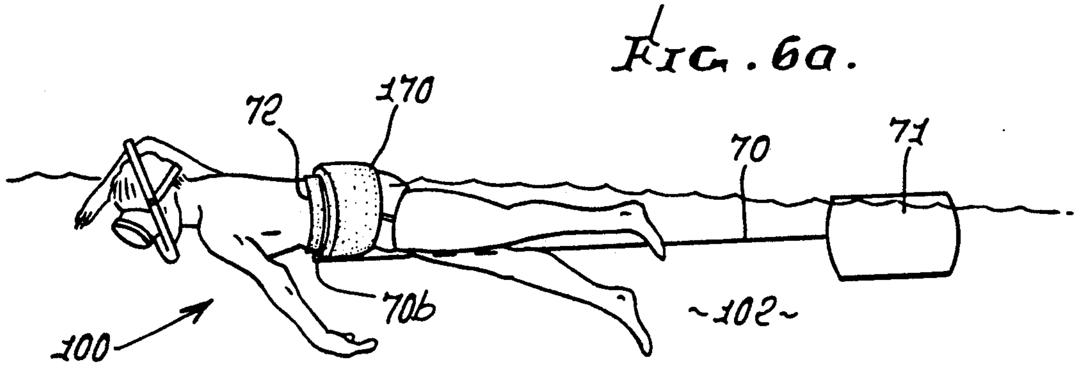
FIG. 6*a* is similar but shows use of a flotation belt.

FIG. 6 is like FIG. 4 and bears the same numbers, but the tether attachment to the harness is at 70*b*, i.e., at the patient's abdomen.

Figure 8:
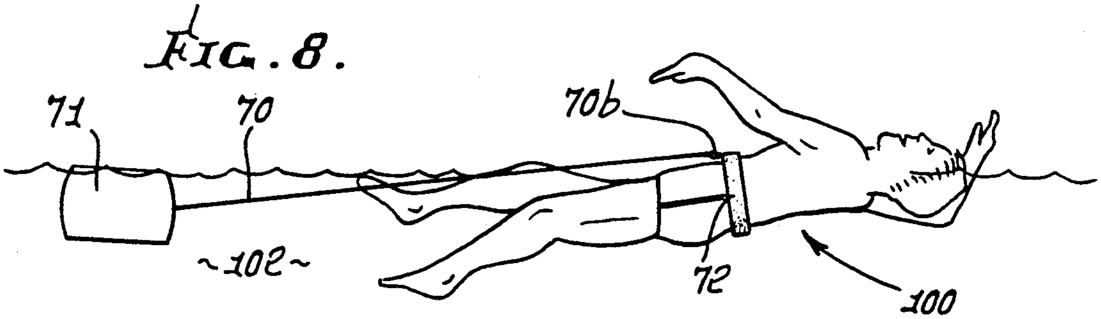
FIG. 8 is a view like FIG. 6 but with the patient facing upwardly.
Figure 8A:
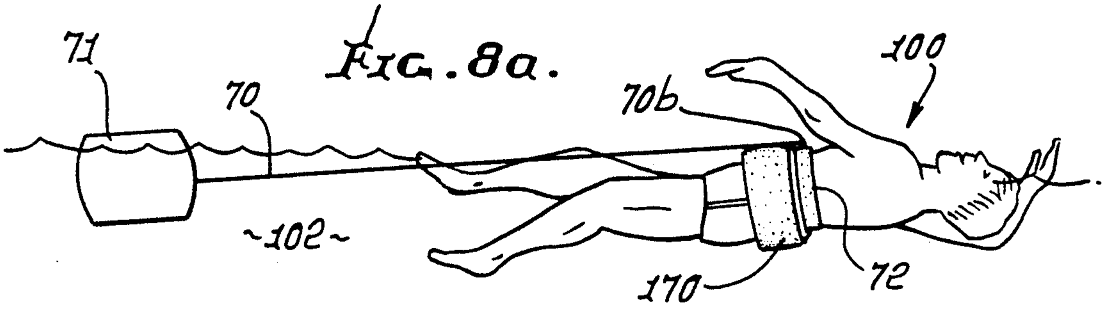
FIG. 8*a* is similar but shows use of a flotation belt.
Figure 10:
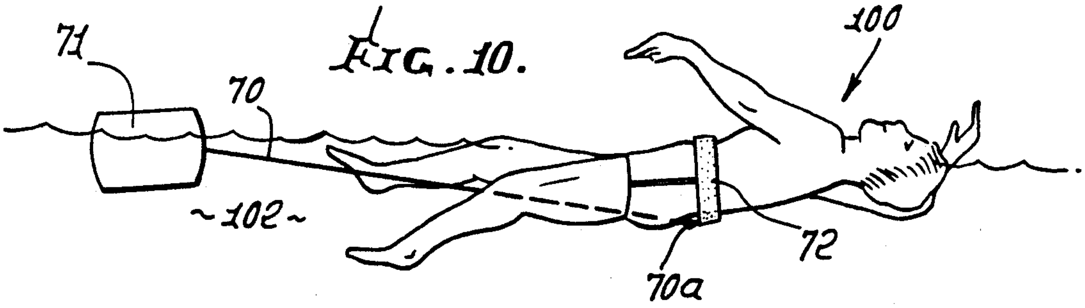
FIG. 10 is a view like FIG. 4 but with the patient facing upwardly.
Figure 10A:
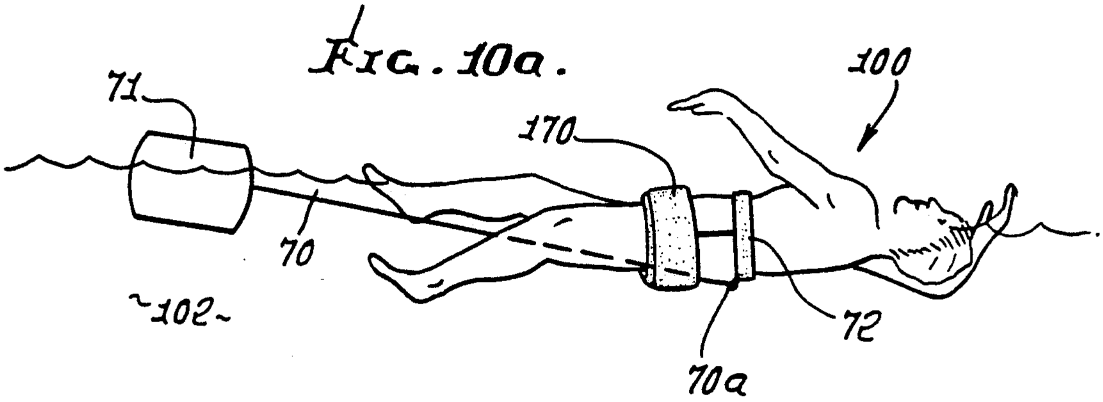
FIG. 10*a* is similar but shows use of a flotation belt.

FIG. 8 is like FIG. 6, but the patient now faces upwardly, i.e., swims on his back; and FIG. 10 is like FIG. 4, but the patient faces upward.

Figure 5:
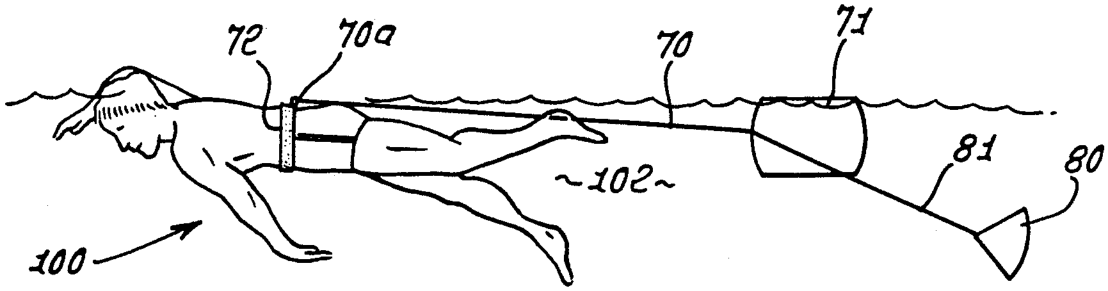
FIG. 5 is a schematic showing tethered attachment of a drag chute to a swimming patient, near the back.
Figure 5A:
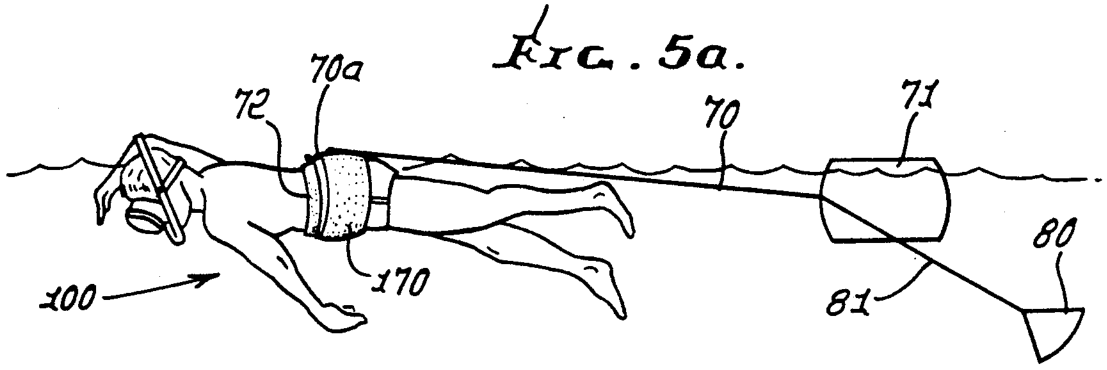
FIG. 5*a* is similar but shows use of a flotation belt.

FIG. 5 is like FIG. 4, but a drag chute 80 is also connected to the tether 70, via a sub-tether 81, to assist in creating drag as the patient swims.

Figure 7:
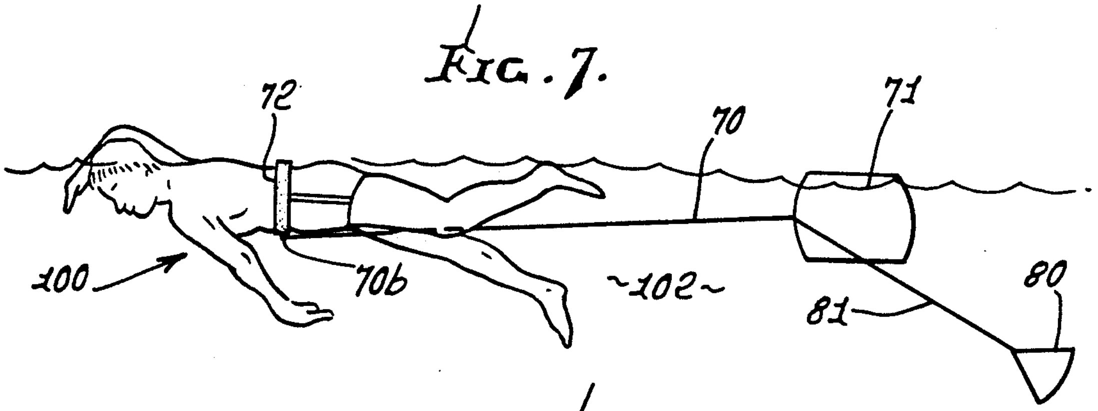
FIG. 7 is a schematic showing tethered attachment of a drag chute to a swimming patient, near the abdomen.

FIG. 7 is like FIG. 6, but again, a drag chute 80 is connected via a sub-tether 81 to the tether 70, at point 81*a*. The drag chute creates greater spinal decompression.

Figure 9:
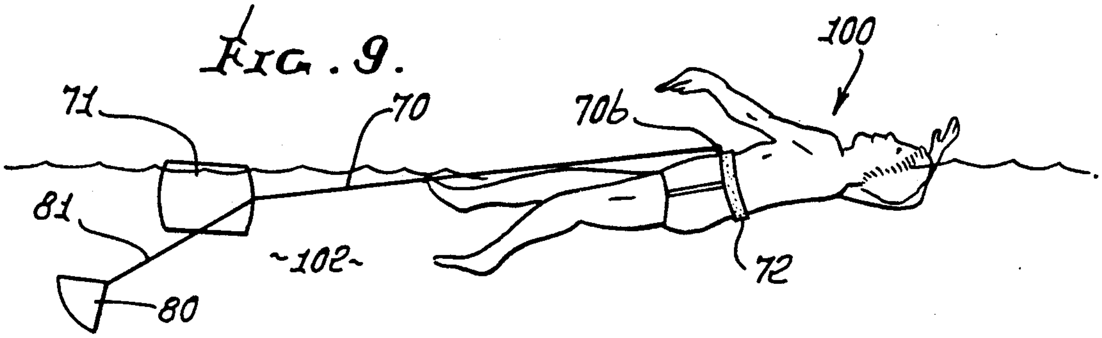
FIG. 9 is a view like FIG. 7 but with the patient facing upwardly.

FIG. 9 is like FIG. 8, but again, the drag chute 80 is connected via sub-tether 81 to tether 70, at point 81*a*.

Figure 11:
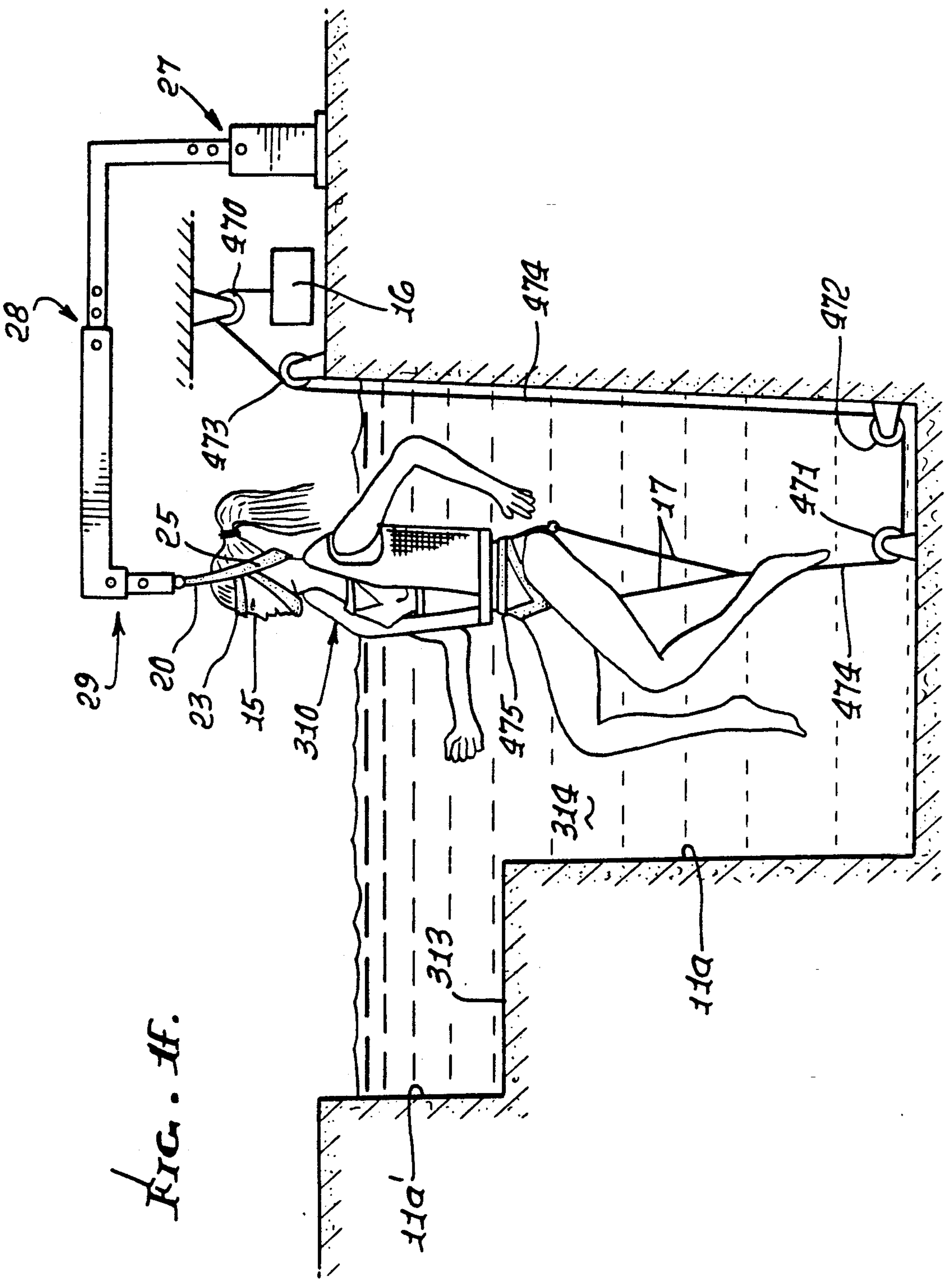
FIG. 11 is a view like FIG. 5 but with the patient facing upwardly.

FIG. 11 is like FIG. 10, but the drag chute is connected via 81 to tether 70, i.e., at point 81*a*. A flotation belt 170 is added or connected to the patient, at waist level to provide more vertical lift (see arrow 91) to assist in spinal displacement. The same belt 170 can be added in any of FIGS. 5–10.

Figure 7A:
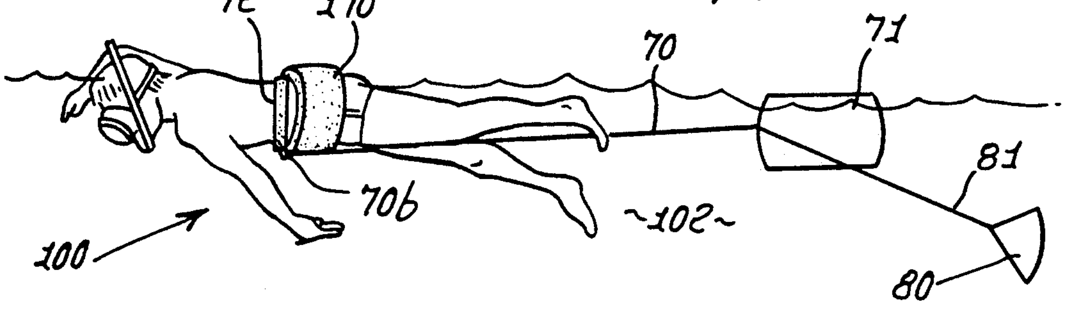
FIG. 7*a* is similar but shows use of a flotation belt.
Figure 9A:
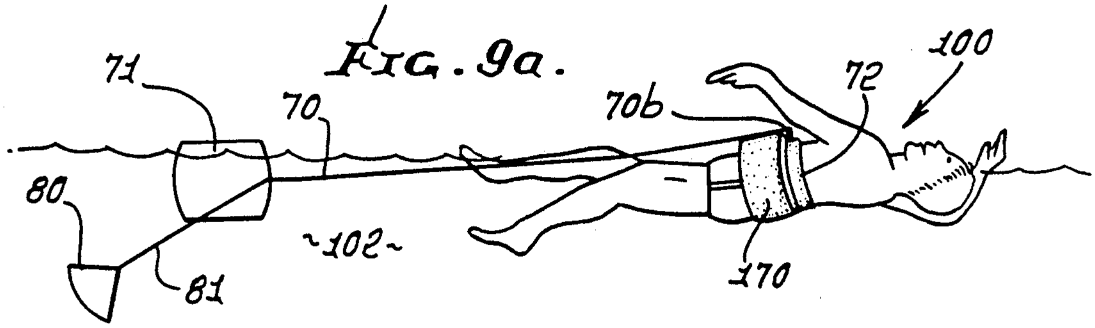
FIG. 9*a* is similar but shows use of a flotation belt.

FIG. 4*a*, 5*a*, 6*a*, 7*a*, 8*a*, 9*a*, 10*a*, and 11*a* correspond to FIGS. 4 through 11, respectively, and show uses of flotation belts 170, as shown. In FIG. 7*a*, the flotation belt aids in spinal decompression. In FIG. 9*a*, the belt 170, at level of the navel and mid lumbar spine, increases lordosis and spinal extension.

Figure 11:
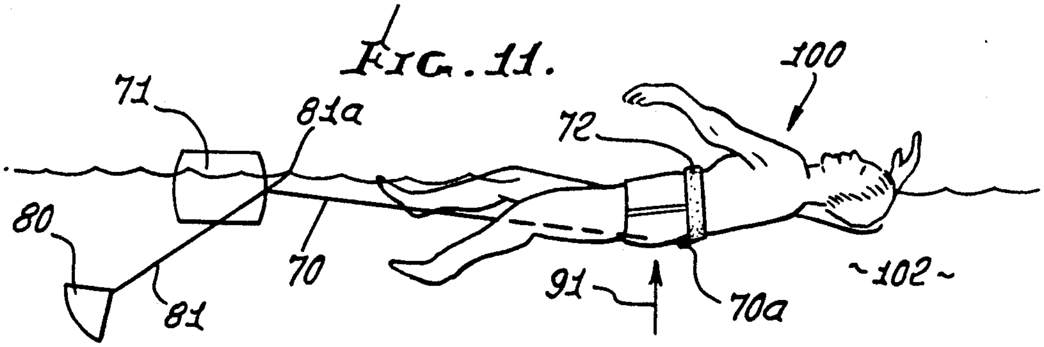
Figure 11A:
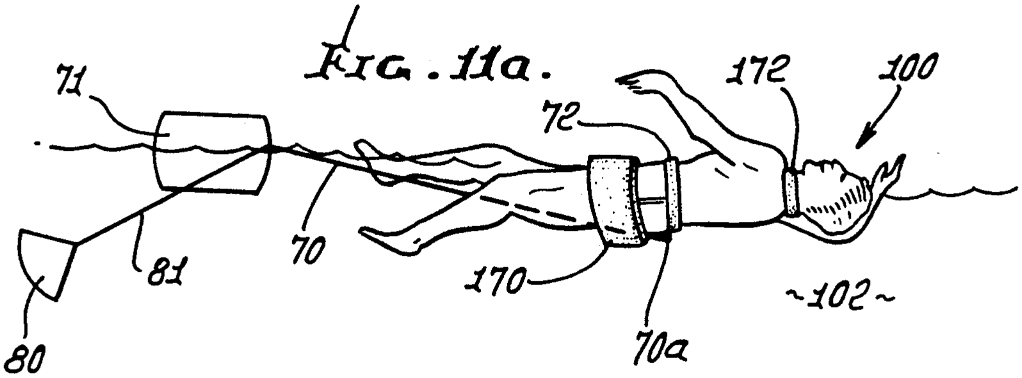
FIG. 11*a* is similar but shows use of a flotation belt.

In FIG. 11*a*, the position of belt 170 at level of pubic bone and mid-lower gluteus maximus decreases lordosis and creates spinal flexion. In FIG. 11*a*, note a cervical flotation pillow indicated around patient's neck. The purpose is to decompress the cervical spine while also helping support the patient by means of flotation, which has a benefit also on the thoracic spine as well as cervical. Other backstroke views can be considered to include such pillows as an option.

In FIG. 12, a human patient 210 is suspended at or above shoulder level, to resist downward pulling force, exerted for example by the body's weight at or below waist level, i.e., providing an equal and opposite upwardly directed force (see arrow 214) exerted on the head 215. These forces are transmitted through the patient's spine, tending to elongate or decompress the spine.

Suspending the body above or at shoulder level is effected as by suspending the patient's head. See bendable tether or band 220 attached to the head, as via a sling 223, and also attached at 221 to the upper end of a lengthwise resiliently yieldable band 222. Attachment of the sling to the head is effected as by strap attachment at 224 to the underside of the chin, or at 225 to the rear of the head or across the forehead, or to any combination of these. Thus, upward froce is transmitted via the upper end of the spine, i.e., at the neck 226.

An illustrtated support frame 227 to support the tether includes end connected members 228–230. Upright adjustable member 228 is a bracket supported at 231 to the top of a door 232. Member 228 is connected at one end to the left end of member 229; and angled member 230 is connected at its opposite ends to members 228 and 229. Pulleys 233 and 234 are supported by member 229, to in turn entrain the tether and reverse its direction, as shown.

The lower end of band 222 is attached to a bracket 236 clipped to the bottom of the door. Thus the band is stretched between bracket 236 and the end of the tether at 221, and resiliently stretches as the tether pulls on it. The band may be looped, and consists of material as disclosed in U.S. Pat. No. 4,544,155.

In operation, as the neck suspended body of the patient moves up and down (as between leg-upright and squat positions), the band variably and resiliently stretches in a smooth and even manner to cushion the variable loading exerted as decompression loading on the patient's spine.

The same arrangement may be established with the patient's body at least partly suspended in a water pool (see water level indicated at 240); and in this case, door 232 may be replaced by a pool side wall, or other support means, to anchor the bracket 236. The patient's arm movement, up and down in the pool water, creates variable vertical loading transmitted via the neck, sling, tether, and stretchable band, to effect the desired variable load decompression on the spine.

The apparatus allows the patient to create varying degrees of cervical/thoracic distraction, therefore decompression of the discs, nerves, blood vessels, vertebrae, and muscular components, while exercising (i.e., performing squats, shoulder movements, etc.). Body movement is accommodated while undergoing traction.

Figure 1A:
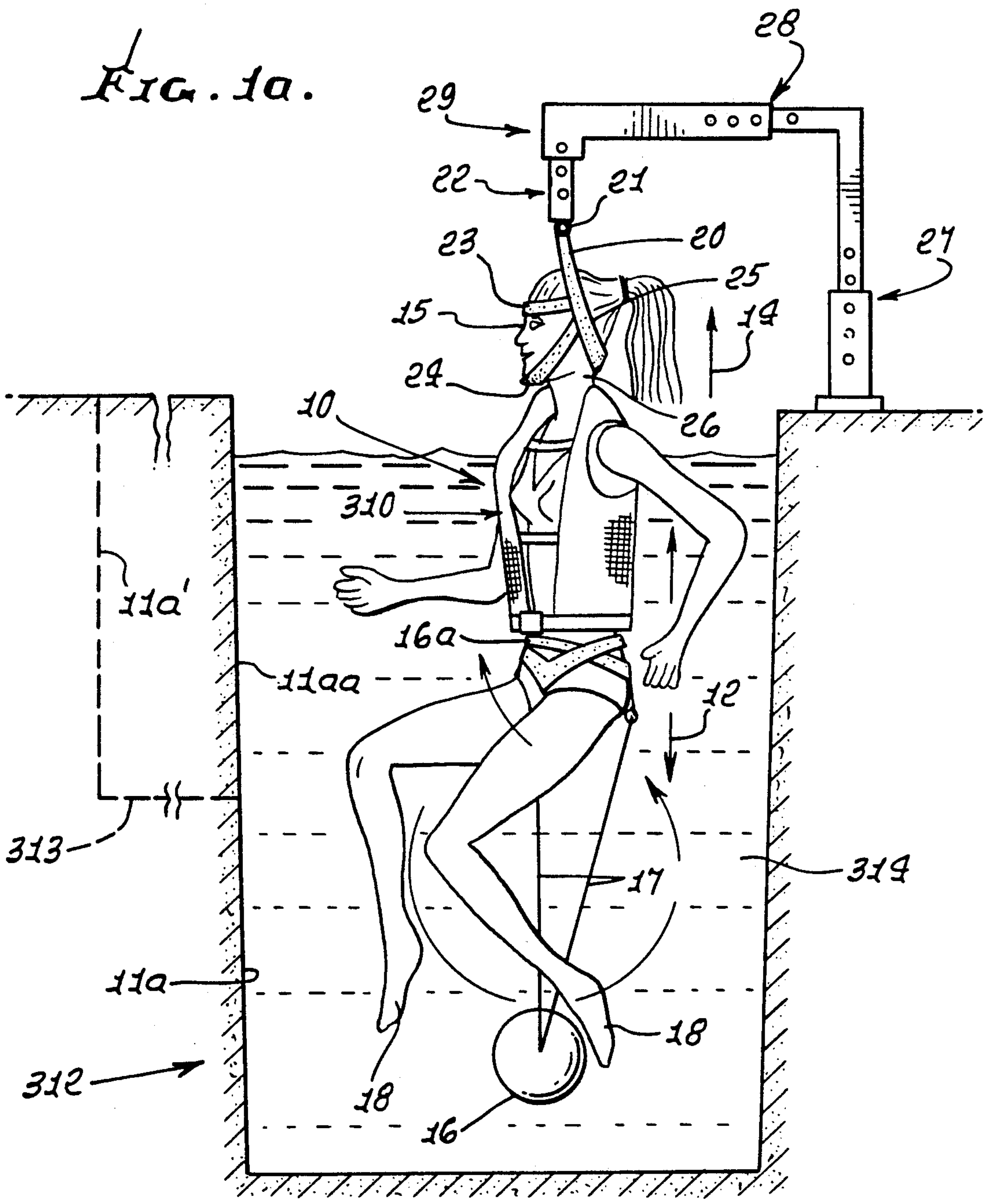

FIG. 1*a* is like FIG. 1 except that the occupant 10 has a float means, such as an inflatable vest 310 attached to his or her trunk to extend at chest or upper back level to exert upward force. The vest is also a safety means. The spa 312 may have a normal bottom surface level 313 and wall 11*a*' offset from the well 314 into which the occupant may step (from bottom 313) for exercise, after which the user may sit on bottom 313. In such an improved spa, wall 11*aa* is eliminated.

Figure 1B:
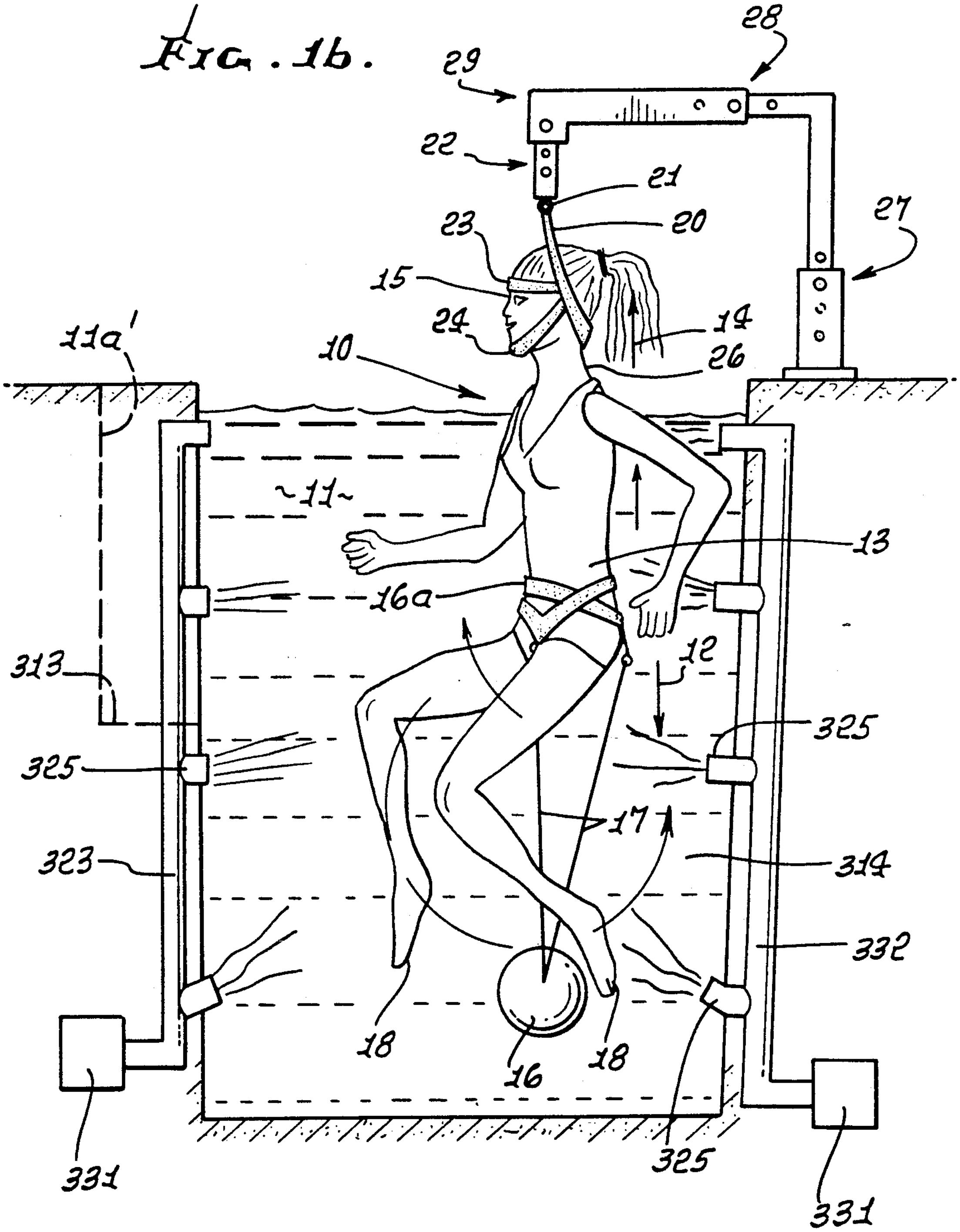

In FIG. 1*b*, the arrangement is like FIG. 1 except that means is proved in association with the spa 312 to jet streams of water (hot or cold) into the spa for hydraulic impingement of the occupant while exercising. See water jet tubes 325 at different levels, and supply sources and ducts 331 and 332.

Figure 1C:
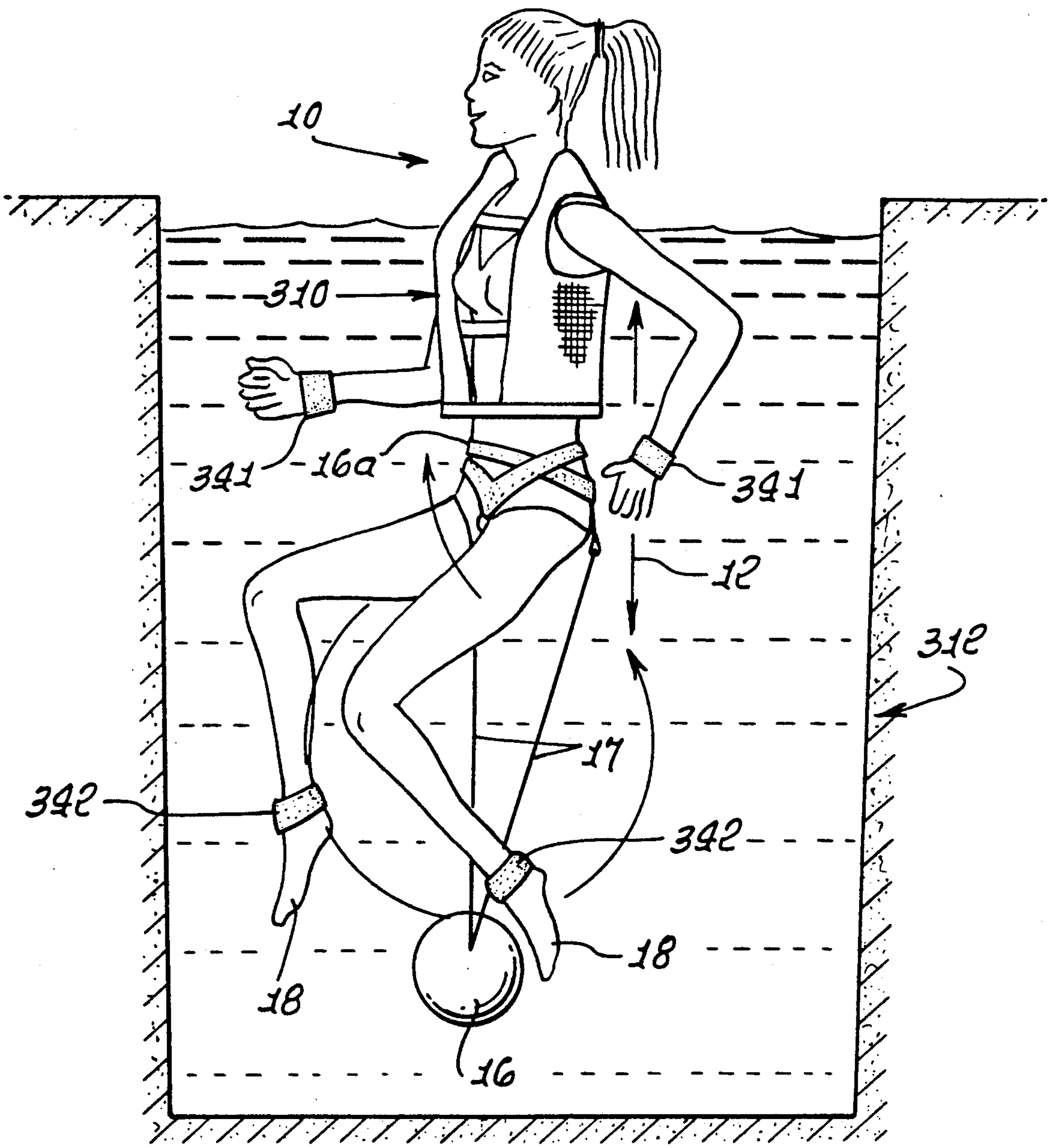

FIG. 1*c* is like FIG. 1*a* except that the patient's neck is not suspended, and weights 341 and 342 are attached to the exercising occupant's wrist and ankles to provide greater resistance to arm and leg movement. This enhances cardiovascular, aerobic activity, and enables muscular reeducation. The weights can be used unilaterally, bilaterally, ipsilaterally, or counterlaterally for muscle reeducation and spinal decompression.

Figure 1D:
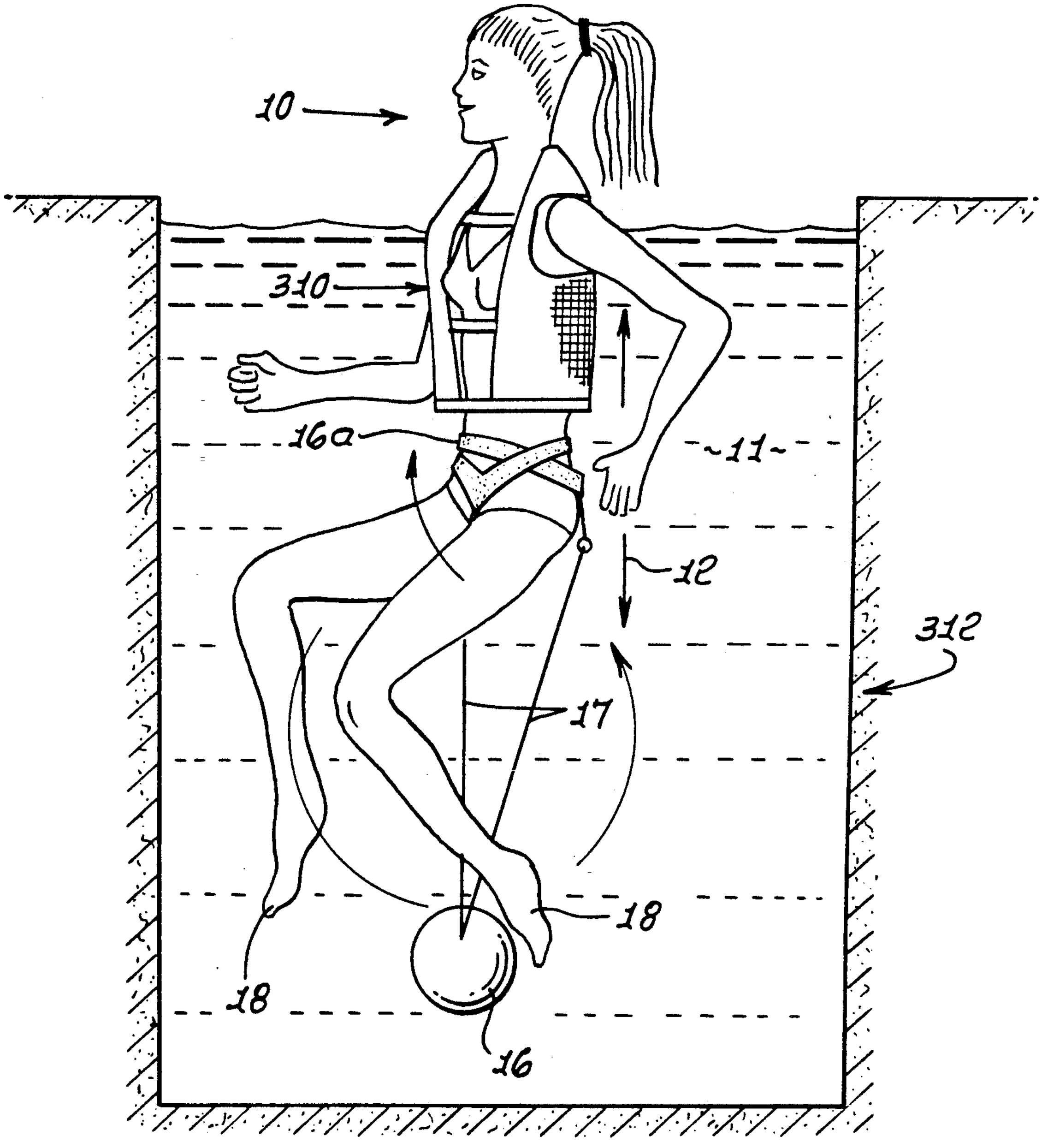

FIG. 1*d* is like FIG. 1*a* except that the neck is not suspended, and an inflatable vest 310 is again employed.

The flotation vest supports the upper body creating a vertical stretch in opposition to the waist straps of which the tethers are attached inferiorly. Both together create spinal distraction decompressing the spine, reducing pressure in vertebrae disc, nerves, muscles, and associated anatomy. They also allow the patient to move freely in the pool water with cardiovascular benefits.

Figure 1E:
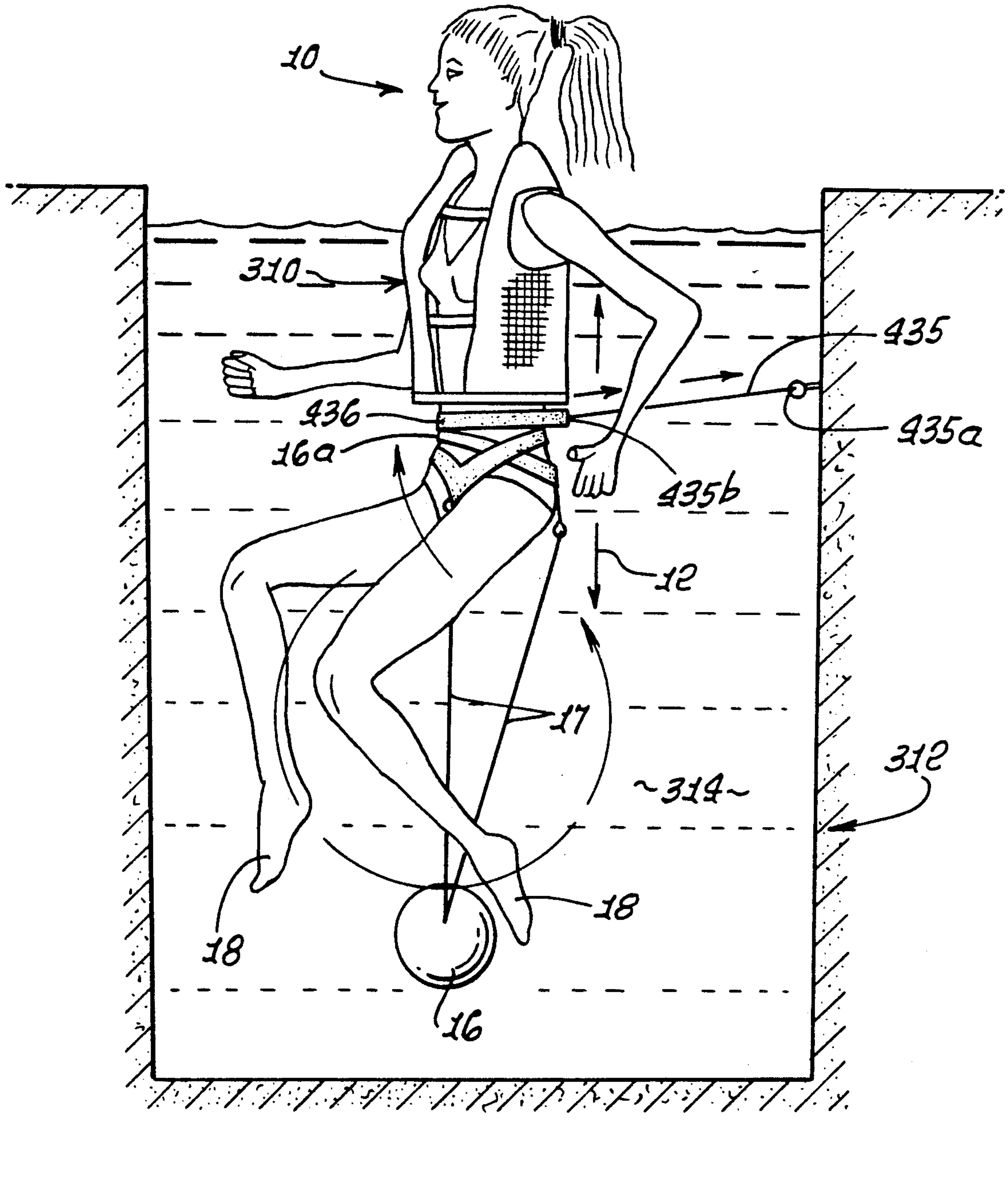

FIG. 1*e* is like FIG. 1*d* except that a horizontal tether 435 is attached at one end 435*a* to the spa wall 11*a*, and at its opposite end 435*b* to a waist strap 436 encircling the occupant. The waist strap helps create further spinal decompression as the patient's body moves away from the wall to which it anchored. The result is decreased lumbar lordosis or sway back.

Note: The elasticity of the tether creates an intermittent traction which aids in spinal decompression and muscular reeducation.

FIG. 1*f* is like FIG. 1*e* except that the weight 16 is now located outside the spa at surface level for suspension as from a pulley 470. Pulleys 471, 472, 473, and 473*a* direct a cable 474 from the weight to the patient's belt 475 to exert downward force as before. The weight is adjustable and may be quickly disconnected if need be.

Figure 1G:
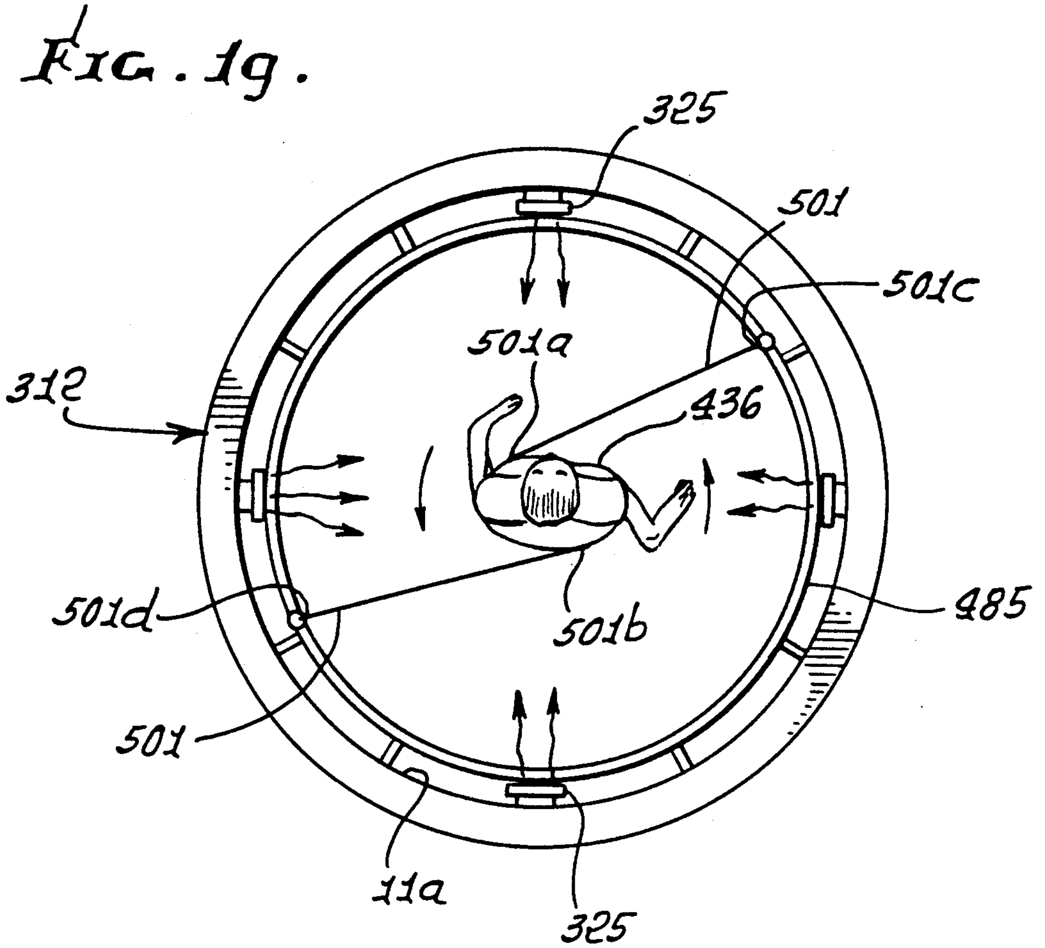

FIG. 1*g* is like FIG. 1*e* except that multiple tethers 501 are connected to the occupant's belt 436 (as in FIG. 1*e*), but at diametrically opposite locations 501*a* and 501*b*. The opposite ends of the tether are attached at 501*c* and 501*d* to the handrail 485 connected to the spa walls 11*a*. The tethers are resiliently stretchable to allow rotation of the occupant's body (vertically oriented) in the spa water against resistance exerted by the tethers. Spa water jets 325 are used, as before. This is beneficial in muscle reeducation for rotary scoliosis and over-developmental activities created or developed from leg length discrepancy (joint instability or any disease process which may have created hypotrophy or hypertrophy of selected muscle groups and therefore created musculor skeletal imbalance).

Figure 3A:
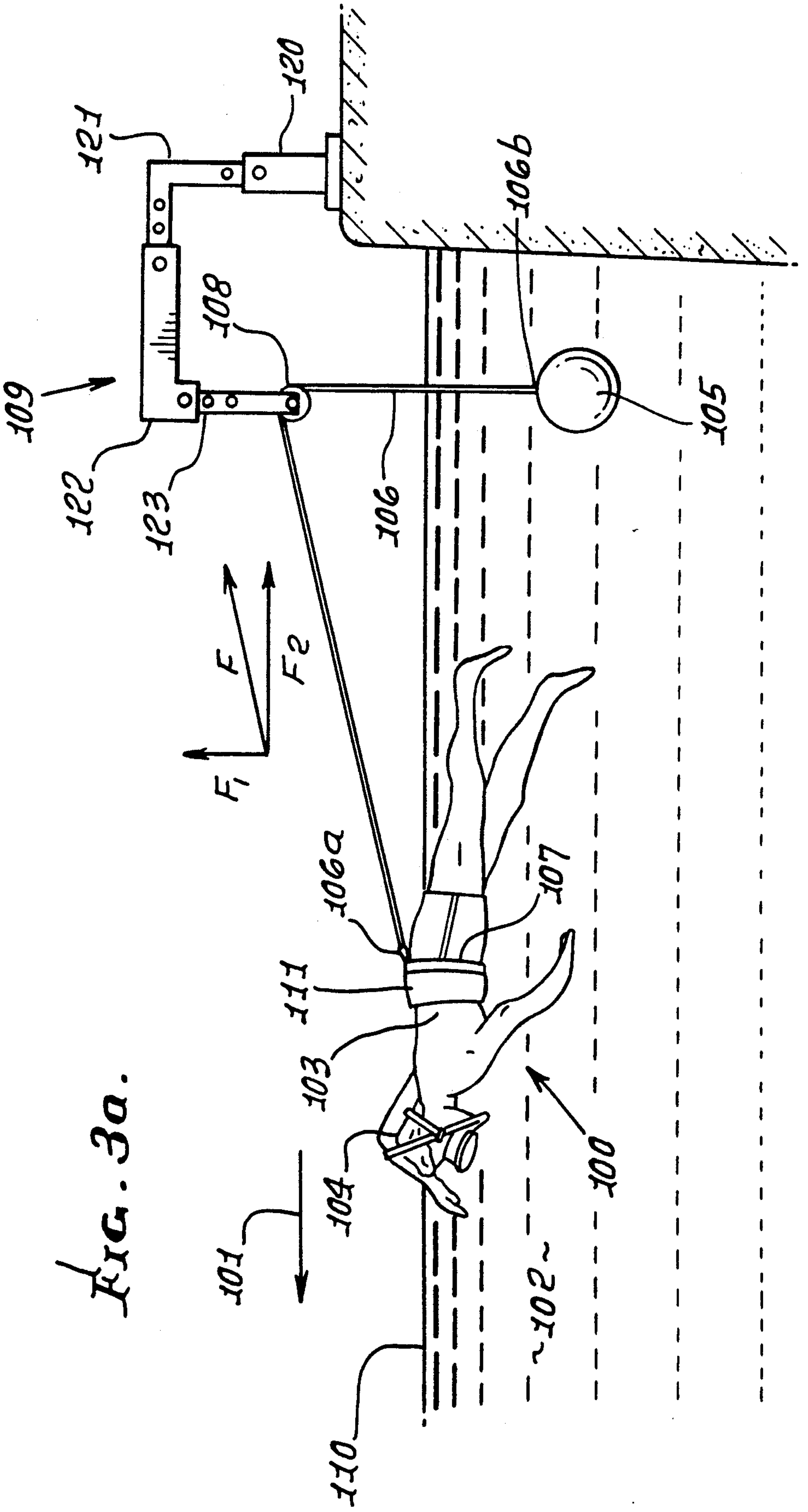
FIG. 3*a* is like FIG. 3 and shows a modification.

FIG. 3*a* is like FIG. 3 except that a flotation belt 111 is attached to the patient to exert upward force on the spine as the patient swims.

In all cases, cardiovascular benefits result from aerobic activity of walking, running and bicycling in the pool or any variation thereof.

Figure 1H:
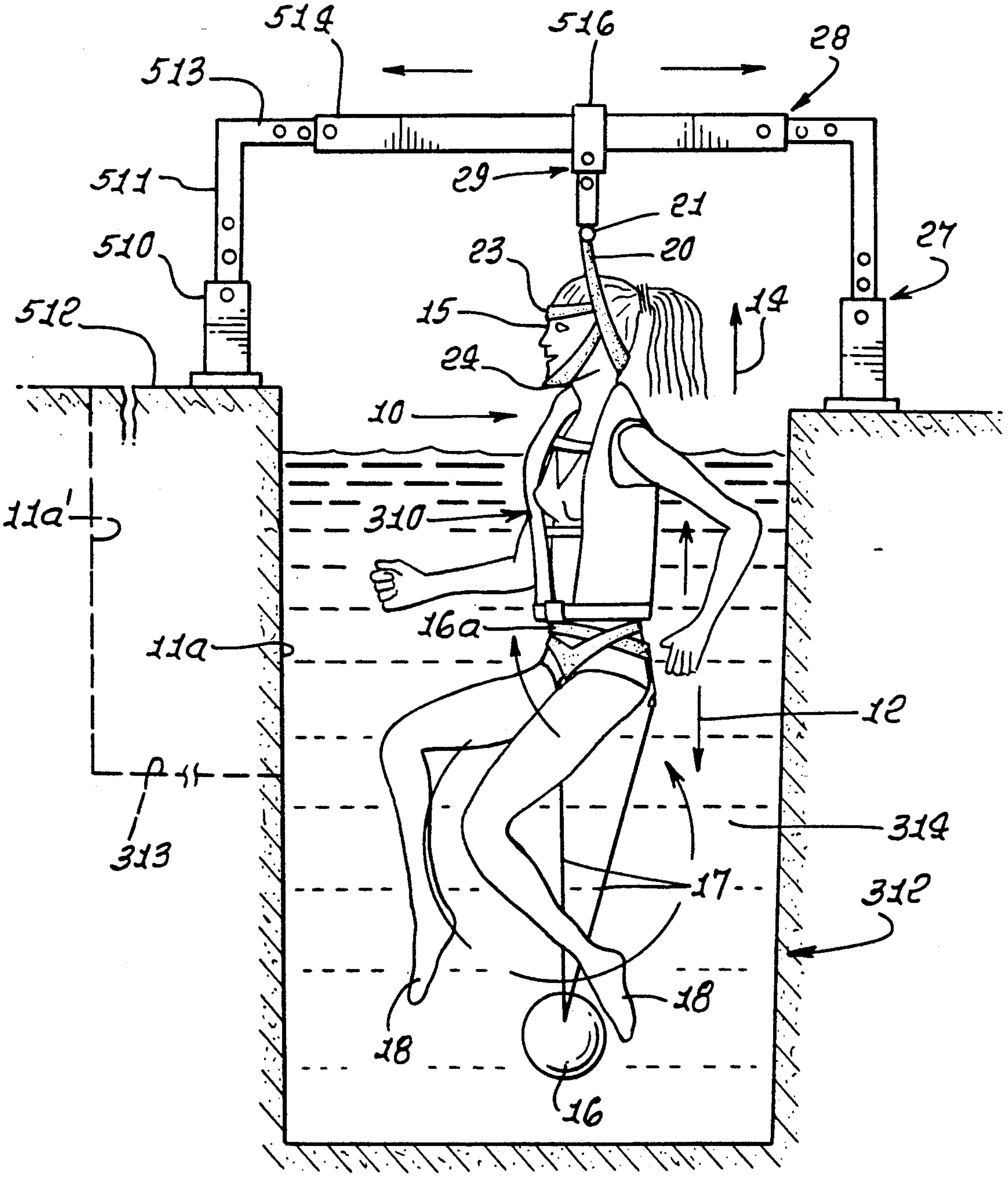

FIG. 1*h* shows elements like those seen in FIG. 1*a*, and similarly identified; however, there is also shown a fixed support means in the form of a vertically adjustable member 510 and 511 carried by fixed surface 512, and horizontally adjustable members 513 and 514. The latter is connected to member 28, to provide a relatively horizontally extending rail. A slider 516 is carried by the rail for movement therealong, forwardly and rearwardly, in response to reactive forces created by movement of the occupant's arms and/or legs in the water body, providing for further cardiovascular aerobic activity.

Figure 1I:
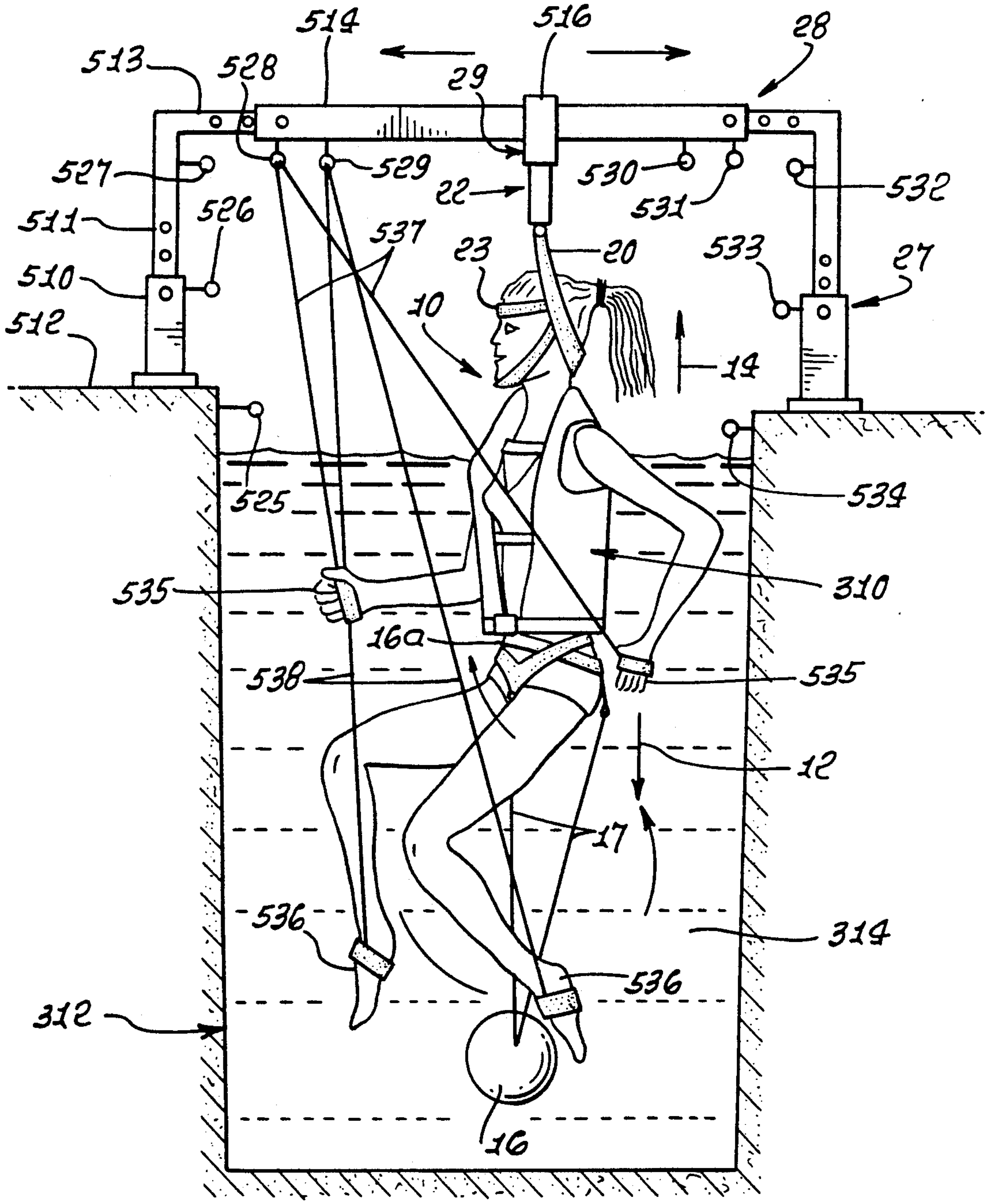

FIG. 1*i* shows elements like those seen in FIG. 1*h*, and similarly identified; however, there is also shown fixed support structure, such as one or more support rings, as indicated at 525–534 on fixed members or structure, as shown, and associated with the spa.

Tether means extends from one or more of the following i) one hand 535 of the occupant
ii) both hands 535 of the occupant
one foot 536 of the occupant
iv) both feet 536 of the occupant to the fixed structure. See for example tether 537 extending from one hand 535 to ring 528, and then to the other hand 535; and also see tether 538 extending from one foot 536 to ring 529, and then back to the other foot. Movement of the arms and hands in the water creates forces acting, via the tether 537 and ring 528, to urge the occupant's suspended body forwardly, as accommodated by the slider 516 on the rail. Similarly, movement of the occupant's legs and feet creates forces acting, via tether 538 and ring 529, to urge the occupant's suspended body forwardly, as accommodated by the slider, on the rail. If one or both tethers are connected to one or more of the rings 530–534, and then moved, as described, the slider 516 will tend to move reversely on the rail.

The tethers may be formed of elastic material to stretch and thereby aid such force creation. This allows for a full range of motion exercises, and/or isokinetic exercises, to duplicate climbing, bicycling, crawling, running, walking, and combinations thereof; this in turn achieves muscle reeducation, and joint and spinal decompression. The tethers can be attached to other points of the body that are movable.

Referring to FIG. 13, structure 11, 11*a*, 11*b*, 20, 21, 22, 23, 29 and 27 the same as in FIG. 1 bears the same numbers, and its use is the same as that described above in connection with FIG. 1. An elongated pool 312*a* is here combined with the spa 312, the two bodies of water therein being in open communication at region 312*b*. This permits the occupant to extend his or her body horizontally, as in a swimming configuration as shown. A belt 360 is attached about the waist of the occupant or user 361, and a tether 362 is attached to that belt and extends to an upright retainer 363, at point 363*a*. The retainer or holder 363 has vertically adjustable parts 364 and 365 which may extend in telescoping relation as shown. Retention point 363*a* is of sufficient height to exert an upward component of force, via the tethers, on the user or swimmer 361 who exerts force on the tether by swimming toward the spa 312. Such exercise produces therapeutic spinal decompression. Accordingly, the total unit 312 and 312*a* provides multiple benefits, as described in connection with FIGS. 1 and 3.

FIG. 12*a* shows an adjustable height bracket assembly where parts 230 and 229 are selectively vertically supported on pegs 227*a*.

I claim:

1. The method of treating a patient having a spinal condition for which traction is recommended, and while the patient's legs and arms remain free for flexing in a water pool, that includes:

a) suspending the patient's body to hang generally vertically in a water pool, and maintaining the body and legs below the waist unsupported other than by buoyancy in the pool, whereby the legs are free to be flexed throughout their lengths, b) said suspending including exerting downward pulling on the patient's body, at waist level, said exertion of downward pulling including attaching a tether to the patient's body at the waist to hang downwardly in the pool, and attaching a movable weight to the lowermost end of the tether and allowing the weight to hang freely in the water pool below the body, spaced from the legs and feet, and at all times in vertical alignment with patient's trunk, in spaced relation to and away from the trunk and feet, and to move about with the body in all directions in the pool, c) and said suspending including freely suspending the patient's body at neck level, acting to resist said downward pulling, as the body moves up and down and rotates in the pool and thereby create force transmission tending to decompress the patient's spine, d) and rapidly flexing the legs throughout substantially their entire lengths to create forces moving the body and weight horizontally in the pool.

2. The method of claim 1 wherein said suspending of the body at neck level is effected by attaching a second tether to the head.

3. The method of claim 2 wherein said attaching of the tether to the head includes at least one of the following:

i) attaching the tether to the rear of the head,
ii) attaching the tether to the chin,
iii) attaching the tether to the upper portion of the head.

4. The method of claim 1 including attaching weight to the patient's arms.

5. The method of claim 2 including providing a horizontally movable support frame to extend above the patient's head, and also attaching the second tether to the support frame.

6. The method of claim 5 including adjusting the support frame, vertically, to displace the patient vertically, and thereby adjust his buoyancy in the pool, and adjust the force transmission tending to elongate the spine.

7. The method of claim 6 wherein said adjusting of the support frame is effected cyclically, to bodily move the patient and cyclically vary the force transmission tending to elongate the spine.

8. The method of claim 1 including producing waves in the pool water which impact the patient and cause body movement, cyclically and bodily, during said suspending steps.

9. The method of claim 2 wherein said suspending includes e) providing a yieldably stretchable band, and anchoring one end of the band, f) and attaching the other end of the band to the second tether, so that loading applied to the second tether by the patient's body is transmitted to the band, tending to stretch same.

10. The method of claim 9 wherein said downward pulling on the patient's body is also effected by body weight, below waist level.

11. The method of claim 9 including effecting vertical oscillation of the patient's suspended body to vary force application tending to recompress the spine.

12. The method of claim 1 wherein said sub paragraph a) suspending includes providing a suspension means above the patient's head, and allowing generally horizontal travel of said suspension means in response to forces created by movement of the patient's body in the water pool.

13. The method of claim 12 wherein said providing of a suspension means includes providing a rail and a slider device which is slidable generally horizontally, above the water pool, on the rail.

14. The method of claim 12 including providing fixed support structure and tether means extending from at least one or more of the following:

i) one hand of the patient
ii) both hands of the patient
iii) one foot of the patient
iv) both feet of the patient to said support structure, whereby the suspended patient may exert force on said tether means to affect said travel of the suspension means.

* * * * *